United States Patent
Yanchev et al.

(10) Patent No.: US 10,324,047 B2
(45) Date of Patent: Jun. 18, 2019

(54) METHOD FOR ONLINE MEASUREMENT OF A PLASTICIZER IN AN ENDLESS FILTER ROD AND A DEVICE FOR PRODUCING AN ENDLESS FILTER ROD OF THE TOBACCO PROCESSING INDUSTRY

(71) Applicants: Tews Elektronik GmbH & Co. KG, Hamburg (DE); AIGER GROUP AG, Zug (CH)

(72) Inventors: Dimitar Yankov Yanchev, Plovdiv (BG); Udo Schlemm, Hamburg (DE); Rainer Herrman, Hamburg (DE)

(73) Assignee: TEWS ELEKTRONIK GMBH & CO., KG, Hamburg (DE)

( * ) Notice: Subject to any disclaimer, the term of this patent is extended or adjusted under 35 U.S.C. 154(b) by 1267 days.

(21) Appl. No.: 14/353,304

(22) PCT Filed: Oct. 26, 2012

(86) PCT No.: PCT/EP2012/004505
§ 371 (c)(1),
(2) Date: Sep. 12, 2014

(87) PCT Pub. No.: WO2013/060476
PCT Pub. Date: May 2, 2013

(65) Prior Publication Data
US 2015/0012228 A1 Jan. 8, 2015

(30) Foreign Application Priority Data
Oct. 26, 2011 (EP) .................................... 11008569

(51) Int. Cl.
*G01N 22/00* (2006.01)
*A24C 5/34* (2006.01)
*A24D 3/02* (2006.01)

(52) U.S. Cl.
CPC ........... *G01N 22/00* (2013.01); *A24C 5/3412* (2013.01); *A24D 3/0295* (2013.01)

(58) Field of Classification Search
None
See application file for complete search history.

(56) References Cited

U.S. PATENT DOCUMENTS

| 2,794,239 A | * | 6/1957 | Crawford | ............... | A24D 3/022 |
| | | | | | 131/343 |
| 3,744,108 A | * | 7/1973 | Greve | .................. | A24D 3/0295 |
| | | | | | 242/417.3 |

(Continued)

FOREIGN PATENT DOCUMENTS

| DE | 102011006414 A1 * | 10/2012 | ........... A24C 5/3412 |
| DE | 102011006416 A1 * | 10/2012 | ........... A24C 5/3412 |

(Continued)

OTHER PUBLICATIONS

STIC Search History and STIC Search Results.*

(Continued)

*Primary Examiner* — Janet L Suglo
*Assistant Examiner* — Leonard S Liang
(74) *Attorney, Agent, or Firm* — Stuart H. Mayer; Mayer & Williams PC

(57) ABSTRACT

A method for online measurement of a plasticizer in an endless filter rod, includes: measuring a resonance shift (A) and line broadening (B) with a microwave resonator at a passing endless filter rod, determining a mass per length of plasticizer from the measurement variables (A, B), measuring a reference mass of plasticizer applied per time with the application of the plasticizer onto the filter tow band, determining an averaged reference mass per length of plasticizer from the measured mass applied over a time period, averaging the values for mass per length of plasticizer, determined using the measurement variables over the same time (Continued)

in which the reference mass of plasticizer is determined, determining a deviation between the averaged reference value for the mass per length and averaged mass per length and correcting the mass per length, determined from the measurement variables of the microwave resonator, according to the determined deviation.

20 Claims, 5 Drawing Sheets

(56) References Cited

U.S. PATENT DOCUMENTS

| | | | | |
|---|---|---|---|---|
| 3,974,007 | A * | 8/1976 | Greve | A24D 3/0295 |
| | | | | 156/378 |
| 4,344,382 | A * | 8/1982 | Hausler | A24D 3/022 |
| | | | | 118/325 |
| 4,368,688 | A * | 1/1983 | Grumer | A24D 3/022 |
| | | | | 118/325 |
| 4,486,186 | A * | 12/1984 | Grumer | A24D 3/0295 |
| | | | | 242/131 |
| 4,497,276 | A * | 2/1985 | Sullivan | A24D 3/022 |
| | | | | 118/325 |
| 4,848,370 | A * | 7/1989 | Federle | A24C 5/1871 |
| | | | | 131/84.1 |
| 5,039,947 | A * | 8/1991 | Kraszewski | G01N 22/04 |
| | | | | 324/634 |
| 5,060,664 | A * | 10/1991 | Siems | A24C 5/3412 |
| | | | | 131/84.1 |
| 5,116,298 | A * | 5/1992 | Bondanelli | A24C 5/34 |
| | | | | 131/906 |
| 5,377,697 | A * | 1/1995 | Deutsch | A24C 5/3406 |
| | | | | 131/330 |
| 5,554,935 | A * | 9/1996 | Kraszewski | G01G 3/16 |
| | | | | 324/633 |
| 6,163,158 | A * | 12/2000 | Moeller | A24C 5/3412 |
| | | | | 324/633 |
| 6,452,404 | B2 * | 9/2002 | Moeller | G01N 22/00 |
| | | | | 324/633 |
| 7,027,148 | B2 * | 4/2006 | Herrmann | A24C 5/3412 |
| | | | | 131/84.1 |
| 7,132,836 | B2 * | 11/2006 | Peters | D01G 31/006 |
| | | | | 324/637 |
| 8,618,817 | B2 * | 12/2013 | Jakoby | G01F 1/662 |
| | | | | 324/452 |
| 2003/0178036 | A1 * | 9/2003 | Demmer | A24C 5/3412 |
| | | | | 131/280 |
| 2003/0206023 | A1 * | 11/2003 | Herrmann | A24C 5/3412 |
| | | | | 324/639 |
| 2005/0096202 | A1 * | 5/2005 | Teufel | A24D 3/022 |
| | | | | 493/39 |
| 2007/0000503 | A1 * | 1/2007 | Herrmann | A24C 5/3412 |
| | | | | 131/280 |
| 2007/0091326 | A1 * | 4/2007 | Schroeder | A24C 5/3412 |
| | | | | 356/625 |
| 2008/0054912 | A1 * | 3/2008 | Herrmann | A24C 5/3412 |
| | | | | 324/640 |
| 2010/0176818 | A1 * | 7/2010 | Herrmann | A24D 3/0295 |
| | | | | 324/640 |
| 2012/0006338 | A1 * | 1/2012 | Herrmann | A24C 5/3412 |
| | | | | 131/105 |
| 2012/0074958 | A1 * | 3/2012 | Schroeder | G01N 22/00 |
| | | | | 324/639 |
| 2014/0043045 | A1 * | 2/2014 | Zaage | A24D 3/0295 |
| | | | | 324/635 |

FOREIGN PATENT DOCUMENTS

| | | | | |
|---|---|---|---|---|
| DE | 102014212497 A1 * | 12/2015 | | A24D 3/0212 |
| DE | 102006041191 C5 * | 8/2016 | | A24C 5/3412 |
| DE | 102017101825 A1 * | 8/2018 | | A24C 5/3412 |
| DE | 102011006414 B4 * | 10/2018 | | |
| EP | 0791823 | 8/1997 | | |
| EP | 1197746 A1 * | 4/2002 | | A24D 3/022 |
| EP | 1197746 B1 * | 5/2002 | | A24D 3/022 |
| EP | 1325683 | 7/2003 | | |
| EP | 1325683 A2 * | 7/2003 | | A24C 5/3412 |
| EP | 1325683 B1 * | 7/2005 | | A24C 5/3412 |
| EP | 1480532 | 7/2005 | | |
| EP | 1480532 B1 * | 7/2005 | | A24D 3/022 |
| EP | 1895291 | 3/2008 | | |
| GB | 2489586 A * | 10/2012 | | A24C 5/3412 |
| GB | 2489587 A * | 10/2012 | | A24C 5/3412 |
| JP | 3866714 B2 * | 1/2007 | | A24D 3/022 |
| WO | 03/070030 | 8/2003 | | |

OTHER PUBLICATIONS

Machine Translation for DE102014212497 (Year: 2015).*
Machine Translation for DE102017101825 (Year: 2018).*
Machine Translation for EP1197746 (Year: 2002).*
Machine Translation for EP1325683 (Year: 2005).*
Machine Translation for DE10200641 (Year: 2003).*
Machine Translation for DE102011006414 (Year: 2012).*
Machine Translation for DE102011006416 (Year: 2012).*

* cited by examiner

METHOD FOR ONLINE MEASUREMENT OF A PLASTICIZER IN AN ENDLESS FILTER ROD AND A DEVICE FOR PRODUCING AN ENDLESS FILTER ROD OF THE TOBACCO PROCESSING INDUSTRY

BACKGROUND OF THE INVENTION

The present invention relates to a method for online measurement of a plasticizer in an endless filter rod of a filter rod maker. The invention relates also to a device for producing an endless filter rod in the tobacco processing industry.

EP 1 325 683 A2 discloses a method and a device for producing a fiber strand of the tobacco processing industry from a filter material having at least three components. The filter material is combined into an endless filter rod using an inlet funnel, and the proportions of the three components in the fiber strand are determined. For measuring the proportions, at least one portion is measured using electromagnetic waves in a first wavelength range, while a further portion is measured using electromagnetic waves in a second wavelength range. In addition, a microwave measurement system with a measuring head is provided that has a microwave source and a microwave detector. Two values are measured and evaluated at the microwave measurement system; this permits a statement to be made about the proportion of water and the common proportion in the strand of the chemically similar components, plasticizer and filter tow. The measurement method according to EP 0 791 823 A2 is used here. The measurement method can be used only where different material components can be detected by separate frequency ranges.

EP 1 895 291 A1 discloses a filter rod measuring station which is equipped with a measuring unit that measures at least the mass of a filter rod and the pressure drop of the filter rod, wherein a microwave measuring device is provided for measuring the mass of the plasticizer and/or the moisture content and/or the dry mass of the filter rod. These are at-line measurements, in which the sample to be measured is removed from the production process in order to deliver it for measuring the filter rod mass, the pressure drop of the filter rod and to the microwave measuring unit. Thus, only a minuscule part of the produced mass can be detected by the at-line operation.

U.S. Pat. No. 7,027,148 B2 discloses a method and a device for determining the triacetin content in a filter rod. The device has a filter tow container, a filter tow stretching and relaxation unit and a filter rod shaping unit. Here, the triacetin content in the filter rod is determined with a microwave resonator using the resonance frequency shift and the spread of the resonance line. To determine the triacetin content in this process, the linear relationship between the results acquired from the measurement variables is used, wherein for determining the offset values, the supply of triacetin is switched off periodically, and the endless filter rod produced without triacetin is measured as a reference value. Because these filter rods without triacetin must be treated as rejects, frequent taring often leads to unacceptable material consumption. Alternatively, a second microwave measurement unit along with speed sensors can be used for measuring reference values before the addition of triacetin; however, this drives up the cost for measuring triacetin sharply.

EP 1 480 532 B1 discloses a device for simultaneous, continuous measurement and regulation of the acetate and triacetin content in filter rods in the cigarette industry. Here, sensors are used for detecting the mass flow of filter tow material, and sensors are used for detecting the sum of the mass flow of filter tow material and plasticizer mass. With the production of the cigarette rods, sensors for measuring the mass flows are coupled in such a way that both the filter material mass and the plasticizer mass can be measured and regulated independently of each other. This measuring technique as a combination of two microwave units and a speed sensor also makes the measurement disproportionately expensive.

In the production of filter rods, generally several material parameters vary independently of each other:

a) The surface density of the filter tow material, that is, the filter tow mass per rod length. The surface density varies typically within short distances, and also occurs within a filter rod.

b) The titer of the filter tow varies with a change of the material used for the filter tow. The titer is typically specified as mass per fiber, and total mass per fiber band relative to a defined length. Due to defects during the production process, as a consequence of a filament breakage in the filter tow band, the total mass of the fiber band can change, so that the number of filaments per band can vary by approximately 2%. These variations can occur suddenly, but remain then over the distance of many filter rods.

c) The moisture of the filter tow material can vary. This variation often occurs slowly over the course of many filter rods, because to a certain extend moisture equalization occurs within the tow bale due to the long storage time.

d) The surface density of freshly applied plasticizer material can vary; triacetin is generally used here. The plasticizer, after hardening, provides the dimensional stability within the filter rod. The variation of the surface density of applied plasticizer material typically occurs over very short distances within a filter rod, and can have strongly fluctuating local concentrations.

e) In addition, during the production, the ratio in the endless filter rod of paper and glue can vary, and in particular the ratio of glue containing water and glue without water can vary. The variation of the ratios of paper and glue, or respectively within the glue, typically occurs relatively slowly within a larger distance over many filter rods.

The previously disclosed online methods for measuring the content of plasticizer in an endless filter rod using a microwave resonator can only inaccurately detect the content of the plasticizer, due to the variation in content, or the methods are uneconomical due to the generation of rejects. Therefore, with all disclosed methods, additional measurement variables are used to reflect these variations, and thus permit a more accurate evaluation of the measurement variables of the microwave resonator. Often, this cannot occur online, as for instance with determining the pressure drop of the filter rod, or it requires further expensive measuring apparatuses at the filter rod maker.

SUMMARY OF THE INVENTION

The object of the invention is to provide a method and a device for online measurement of plasticizer content in an endless filter rod using a simple microwave measuring unit, in order to be able to reliably detect and regulate both short and long term fluctuations in the content of the plasticizer. The method of the invention consists in automatically compensating short-term fluctuations and rapid changes in the process flow, for instance the tow quantity, using the microwave method, whereas long term changes effective over the course of many filter rods, such as that of the moisture or the paper, are corrected through the long term reference measurements.

The object according to the invention is achieved by a device with the features of claim 1. Advantageous embodiments are the subject of the dependent claims.

The method according to the invention is provided and intended for online measurement of a plasticizer in an endless filter rod at a filter rod maker. According to the invention, a resonance frequency shift (A) and a line broadening (B) of the resonance curve is measured at a passing endless filter rod using a microwave resonator. It is generally known in microwave measuring technology that a dielectric material located in the resonator cavity results in a shift in the resonance frequency compared to the empty resonator cavity, and in a broadening of the resonance curve compared to the empty resonator cavity. According to the invention, a mass per length of plasticizer is determined from the two measurement variables of the microwave resonator. For this purpose, it is preferable to assume a linear relationship between the resonance frequency shift and the line broadening, and the mass per length of the plasticizer. According to the invention, a reference measurement is made of the plasticizer that over a longer time period during which many filter rods are produced, relates to the mass of plasticizer applied per time with its application on a filter tow band. Before forming the endless cigarette rod, a filter tow band is present, upon which the plasticizer is applied. With the method according to the invention, the reference mass of the applied plasticizer is measured online during the production of the endless filter rod. According to the invention, an average reference mass per length of the plasticizer is determined from the measured reference mass of applied plasticizer per time. For this purpose, the speed of the filter tow rod in the machine is known, and the reference mass of plasticizer applied per unit time is converted to an averaged reference mass of plasticizer applied per length.

With the method according to the invention, in addition, over the same time period as the determination of the reference mass, an average of the value for the mass per length of the plasticizer is determined, using the measurement variables of the microwave resonator. The microwave resonator can have a very small measurement field of a few millimeters. With the averaging procedure, the values for the mass per length, determined using the measurement variables of the microwave resonator, are averaged over a certain length. According to the invention, a deviation is determined between the averaged value for the mass per length, as it results from the measurement variables of the microwave resonator according to the averaging procedure, and the average reference mass per length, as it results from the reference mass measurement. This deviation is used according to the invention to correspondingly correct the mass values per length determined from the measurement variables of the microwave resonator.

Therefore, with the method according to the invention, using only a single microwave resonator, the mass per length resulting from the measurement variables of the microwave resonator is corrected with the inclusion of the averaged reference mass per length, as results, for instance, from the application of plasticizer onto the filter tow band. An expensive further measuring unit at the cigarette machine is not needed for this purpose. In addition, the correction of the values by the averaged reference mass per length adjusts very gradually and reliably, and can correct fluctuations in the measurement variables of the microwave resonator.

The duration of such long term reference measurement is preferably realized over the production of many filter rods. For the duration, a number of filter rods can be specified, for example. Expediently, this duration should at least amount to the duration of a back and forth run of a lift-off point of the filter tow from the surface of the filter tow bale. Filter tow bales are typically built so that the lift-off point in a layer of the bale runs meandering back and forth. In a layer lying below, the lift-off point then moves perpendicular to the previous layer, meandering back and forth. Because observed moisture differences can occur between the center and surface of the bale, running the lift-off point back and forth is a suitable measure for the time duration in order to equalize the moisture fluctuation within the filter tow bale.

In one preferred embodiment, the mass per length ($m_W$) of plasticizer is calculated according to the following expression:

$$m_W = k0 + k1*A + k2*B + P(\Phi),$$

wherein A is the resonance shift, B is the line broadening, k0, k1, k2 are real numbers, $\Phi$ is the quotient of A and B, and P is a polynomial depending on $\Phi$. The expression above for the mass per length of the plasticizer assumes the already known linear relationship between plasticizer mass and shift of the resonance frequency and the broadening of the resonance curve. In addition, there is a so-called offset value k0 that does not correlate with the measurement variables of the microwave resonator. Furthermore, as an additional correction term, there is a polynomial that depends on quotients from A and B. As is well known in moisture measuring techniques, the quotient B/A depends on the moisture. In the use for determining the mass of the plasticizer, the quotient B/A does not depend solely on the moisture, but also on the mass of the plasticizer. Occasionally, instead of the quotient B/A, a function is used that is also dependent on B/A, a monotonic strictly increasing function in the range of 0 to Pi/2, for instance arctan (B/A). In the present application, the convention is used that B/A can always also indicate the value of arctan (B/A) or another function. The coefficients k0, k1 and k2 and the polynomial P with its coefficients are initially determined during the calibration of the method.

In a particularly preferred embodiment, the value of the constant k0 is corrected proportionally to the deviation. The correction of k0 results therefore from the difference of the averaged "microwave" mass per length and the reference mass per length determined from the plasticizer application.

In a preferred embodiment of the method according to the invention, the plasticizer is applied from a storage container onto the filter tow band, wherein the weight reduction of the storage container is measured for determining the reference mass per time of applied plasticizer. The weight of the storage container decreases continuously with continuous application of plasticizer onto the filter tow band. The reduction in weight corresponds to the reference mass per time of applied plasticizer, if a continuous flow of plasticizer onto the filter tow band is assumed. However, if this flow is not continuous, the time window for determining the reference mass must be appropriately enlarged so that fluctuations in the application intensity of plasticizer are negligible. Using the transport speed of the finished endless filter rod or the count of the filter rods produced in the time window, the mass per time is converted into a mass per length, in that the reference mass per time is multiplied by the rod speed or divided by the number or rods.

In an alternative embodiment of the method according to the invention the plasticizer is applied from a storage container onto the filter tow band, wherein for determining the reference mass per time of applied plasticizer, the reduction of the fill level of the storage container is measured by a continuous fill level gauge. Applying plasticizer onto the filter tow band continuously decreases the fill level of the storage container. As a result, the reference mass of applied plasticizer per time can be calculated just as with the container weight measurement. Here too, using the transport speed of finished endless filter rods or the count of the filter rods produced in the time window, the mass per time is converted into a mass per length.

Alternatively, the volume of plasticizer passing through a feed line to the plasticizer application can be measured for determining the reference mass per time of applied plasticizer. The plasticizer is generally conveyed from the storage container via a feed line to the point of the filter rod maker at which it is applied, using rotating brushes for example. The averaged mass per length of plasticizer can be derived by measuring the volume flow in the feed line and considering the speed of the endless filter rod or the number of filter rods.

With the method according to the invention, the averaged mass per length of plasticizer is continuously determined. Therefore, the averaged mass per length is a continuously recalculated moving measured value.

In a preferred embodiment, the deviation of the reference mass of plasticizer is also continuously determined, and preferably the mass of plasticizer determined from the measurement variable of the microwave resonator is continuously corrected.

In a preferred further development of the method according to the invention, a moisture value for the filter rod is determined depending on the measurement variables of the microwave resonator, and the corrected value for the mass per length of plasticizer is taken into consideration. As already mentioned initially, it is known in moisture measurement technology that the quotient B/A is proportional to the moisture of the measured material. Because during the production of the cigarette filter rods, the mass of the applied plasticizer is also reflected in this moisture value, the moisture value can be improved by considering the mass of plasticizer. By adjusting to the corrected value of the mass per length of plasticizer, a reliable measurement value for the moisture is also obtained.

The moisture value $\Psi$ is preferably determined according to:

$$\Psi = f0 + f1 * \Phi + f2 * m_W$$

wherein f0, f1 and f2 are constants, $\Phi$ is the quotient of the resonance shift A and the line broadening B, and $m_W$ is the corrected mass value of plasticizer.

In a particularly preferred further development of the method according to the invention, the intensity of electromagnetic radiation in the infrared or visible wavelength region scattered on the fibers of the filter tow strand is also measured. In contrast to the microwave measurement, the dielectric properties of the filter tow band are not used here, but rather the surface properties with the scattering. Depending on the measured intensity S, an additive correction term is calculated for the mass per length of plasticizer determined from the microwave variables. This further development of the method is based on the realization that the measurement variable $\Phi$ of the microwave resonator depends substantially on the mass of plasticizer and the moisture in a filter tow strand, but the tow mass has little influence. In contrast, if the intensity of laser light is used as an electromagnetic radiation, when this is scattered in the filter tow band, then the intensity is more strongly diminished when more fibers are located in the beam path. Therefore, this variable is solely dependent on the total tow fiber surface in the beam path, and does not depend, or depends only slightly, on the moisture content and the applied plasticizer. By considering the laser signal intensity, the method according to the invention can lead to a still improved independence of the microwave-triacetin value of the titer of the tow material.

To reflect the change of the filter tow material and the associated changes in the titer, a further additive correction variable for the mass per length of plasticizer, determined from the measurement variables of the microwave resonator, can be determined depending on the titer of the tow material. The mass per length $m_W$ of plasticizer is preferably calculated according to the following expression:

$$m_W = k0 + k1*A + k2*B + P(\Phi) + k3*\log(S*G/F),$$

wherein k0, k1, k2 and k3 are constants, A is the resonance shift, B is the line broadening, $\Phi$ is the quotient of A and B, P is a polynomial function of $\Phi$, G is the mass of the filter tow band, and F is the mass of an individual fiber of the filter tow band with a predefined length. The titer of the tow material is typically specified in the form of "F-Y-G", wherein F is the mass of a fiber, G is the mass of the total band specified in grams with a uniform length, traditionally 9 km. In that the intensity S of the scattered electromagnetic radiation is applied, using the known values G and F from the titer, the corrected mass of plasticizer per length can be determined, which ensures improved independence from the titer with a change of the tow material. It is sufficient to simply enter the variables F and G using the keyboard of the operator terminal at the machine.

For the method according to the invention, triacetin is preferably used as a plasticizer for the endless filter rod; it is preferably applied in fluid form by rotating brushes or by nozzles onto the filter tow band.

The object of the invention is also achieved by a device for producing an endless filter rod in the tobacco processing industry according to claim 16.

The device according to the invention makes it possible to produce an endless filter rod of the tobacco processing industry with an online measurement of the content of plasticizer. The device is equipped according to the invention with a microwave resonator that measures a resonance frequency shift (A) and a line broadening (B) of the passing endless filter rod. Furthermore, a measurement device is provided that measures the reference mass per time, over a longer time period, of a plasticizer applied onto the filter tow band. This longer time period is preferably at least as long as the shortest time period of a periodically occurring moisture variation, that is, the time of a back-and-forth run of the lift-off point of the tow from the filter tow bale. The measured values of the microwave resonator and the reference measurement device are supplied to an evaluation unit. The evaluation unit determines a mass per length of plasticizer from the measured values of the microwave resonator. In addition, the evaluation unit determines a reference mass per length from the measured measurement values of the reference measurement device. According to the invention, the evaluation unit corrects the mass per length of plasticizer obtained from the microwave measurement based on the averaged mass per length of plasticizer, as determined by the reference measurement device. The device is preferably designed to perform the method according to the invention.

In a preferred embodiment of the invention, the reference measurement device is built as a scale which detects a mass change per time for the plasticizer in a storage container. The average reference mass of plasticizer per length can be determined based on the mass change per time, considering the transport speed of the filter tow band or the number of filter rods.

In a further embodiment of the invention, the reference measurement device is built as a continuous fill level measuring device which detects a fill level change per time in a storage container for the plasticizer. This continuous fill level measurement can be built as a capacitive sensor, an ultrasonic elapsed time sensor, a microwave elapsed time sensor, or as a mechanical float sensor. The average reference mass of plasticizer per length can be determined based on the level change per time, considering the calibration curve of the plasticizer container, the transport speed of the filter tow band or the number of filter rods.

Alternatively, or in addition, the reference measurement device is designed as a volume flow meter that detects a volume per time during application of the plasticizer. The averaged reference mass of plasticizer per length can be determined based on the flow rate of plasticizer per time determined over a longer time period, considering the density of the plasticizer, the transport speed of the filter tow band or the number of filter rods.

In addition, a combination of the different methods for the reference measurement of the plasticizer mass per length is possible, in order to attain an improved measurement accuracy of the reference measurement, for instance to detect different operating states in the machine, such as when the storage container of triacetin is automatically filled.

In a further preferred embodiment, a laser is provided in the visible or infrared wavelength range, and an intensity sensor is provided for the laser light scattered at the filter tow band. The evaluation unit corrects the mass per length of plasticizer depending on the measured intensity of the scattered laser light so that a triacetin measurement can be obtained that is independent of the titer of the filter tow.

BRIEF DESCRIPTION OF THE DRAWINGS

The present invention is explained in the following in more detail using an exemplary embodiment. In the figures.

DETAILED DESCRIPTION OF THE INVENTION

Figure 1:
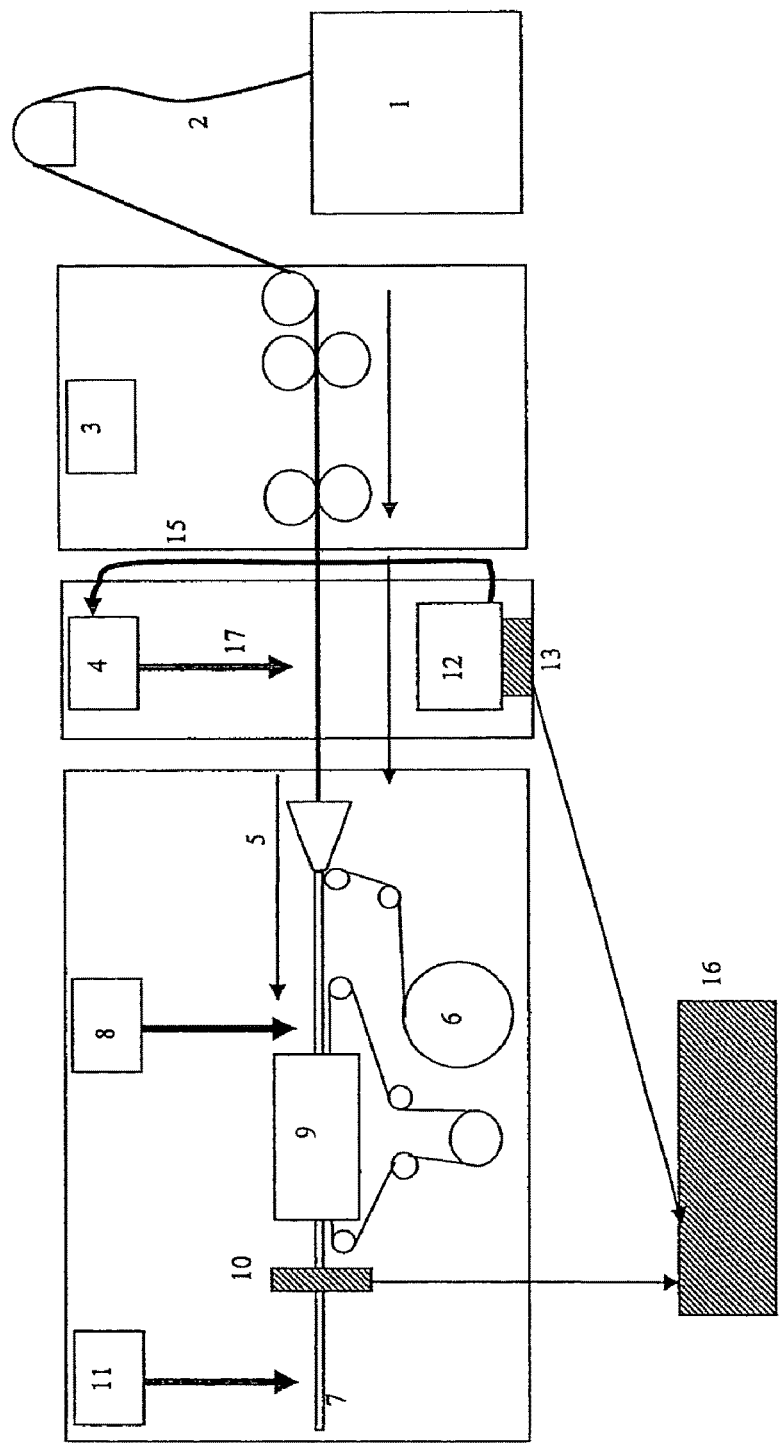
FIG. 1 shows a schematic view of a filter rod maker with a microwave sensor at the endless filter rod and a triacetin reference measurement using a scale for the triacetin container.

FIG. 1 shows a schematic view of a filter rod cigarette maker with a microwave resonator 10 and a triacetin scale 13 for the triacetin reference measurement. The endless cigarette filter rod 7 is produced in a known manner. A filter tow band 2 is supplied from a filter tow bale 1 to a filter tow stretching and relaxation unit 3. After the filter tow band has left the stretching and relaxation unit, the triacetin is applied onto it in a following step. The triacetin 17 is applied onto the filter tow band using the triacetin application 4. The filter tow band is supplied to an inlet funnel 5 for forming the rods. Paper for wrapping the rod is supplied from a paper bobbin 6 to the band running in the inlet funnel 5. Glue 8 is supplied to the partially wrapped filter rod and is hardened in a heating zone 9.

A microwave resonator 10 for measuring is provided after the heating zone 9. The produced endless filter rod 7 is subsequently cut by the cutting device 11 into filter rods.

The triacetin 17 is supplied from a triacetin container 12 that is connected by a supply line 15 to the triacetin application 4. The change of mass in the triacetin container 12 is continuously measured using a scale 13 for determining the reference triacetin mass.

The microwave measurement device 16 evaluates the measurement signals of the microwave resonator 10 and the measured values from the scale 13.

The microwave resonator 10 can be a profile resonator for example, in a particular construction with a very small space requirement, so that it can also be installed subsequently in a filter rod maker. The microwave resonator measures the resonance frequency shift A and the line broadening B of the resonance curve caused by the endless cigarette rod, compared to the empty resonator. Due to the dielectric properties of the endless filter rod, the resonance developed in the microwave resonator is shifted in its resonance frequency and the resonance is broadened.

Figure 2:
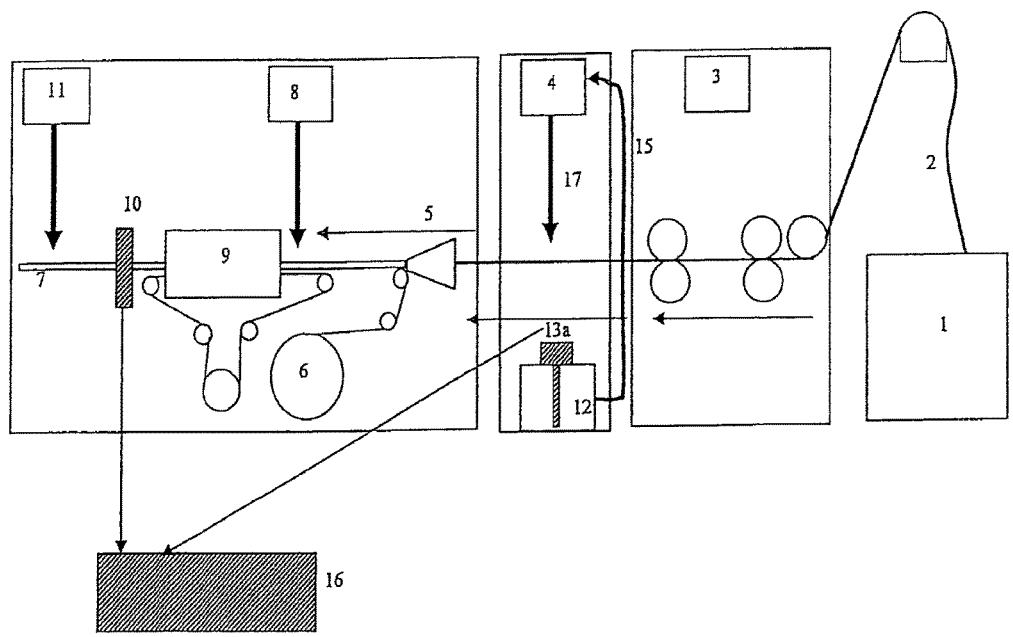
FIG. 2 shows a schematic view of a filter rod maker with a microwave sensor at the endless filter rod and a triacetin reference measurement using a continuous fill level measuring device for the triacetin container.

FIG. 2 shows a schematic representation of a filter rod maker with a microwave sensor 10 at the endless filter rod 7, as shown in FIG. 1. However, the triacetin reference measurement is realized here by means of a continuous fill level measurement device 13*a* for the triacetin container. This continuous fill level measurement can be built as a capacitive sensor, an ultrasonic elapsed time sensor, a microwave elapsed time sensor, or as a mechanical float sensor.

Figure 3:
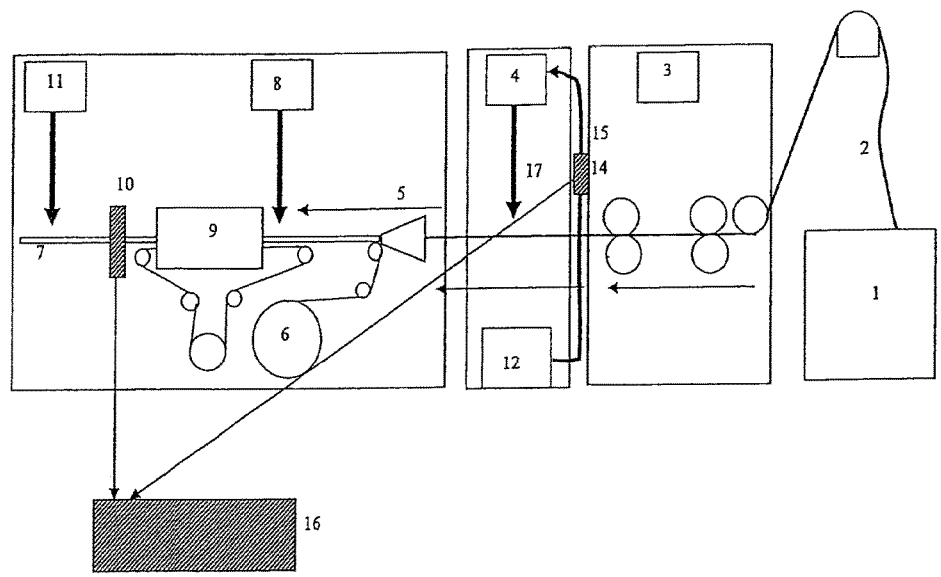
FIG. 3 shows a schematic view of a filter rod maker with a microwave sensor at the endless filter rod and a triacetin reference measurement using a flow measurement in the line between the triacetin container and triacetin application unit.

FIG. 3 shows a schematic representation of a filter rod maker with a microwave sensor 10 at the endless filter rod 7, as shown in FIGS. 1 and 2. However, the triacetin reference measurement is realized here by means of a flow measurement of the volume of the triacetin fluid 14 in the supply line 15.

Figure 4:
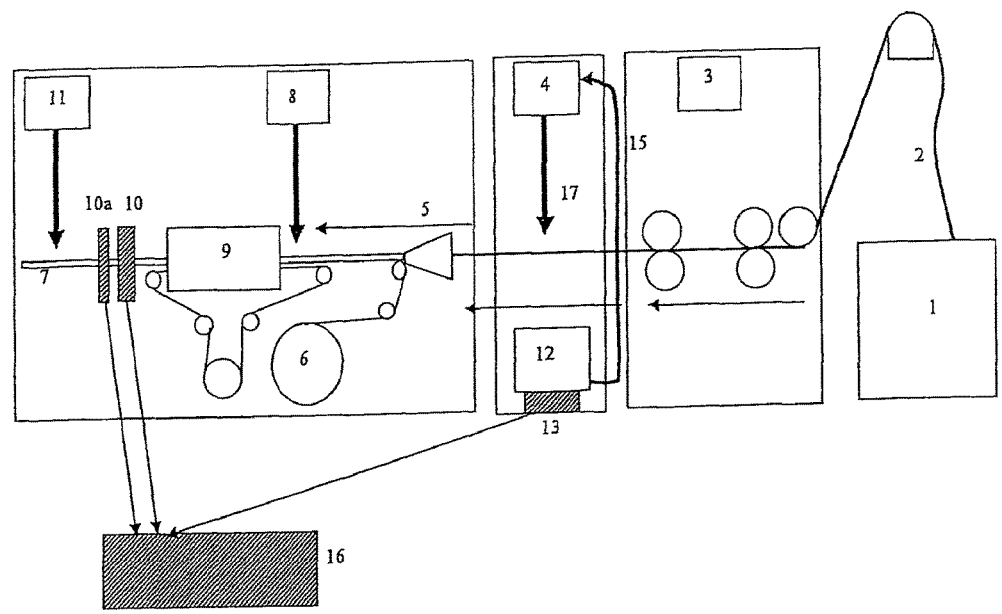
FIG. 4 shows a schematic view of a filter rod maker with a microwave sensor at the endless filter rod, an infrared laser sensor for the improved triacetin correction device for the titer change, and a triacetin reference measurement by means of a scale for the triacetin container.

FIG. 4 shows a schematic representation of a filter rod maker with a microwave sensor 10 at the filter rod 7, as in FIGS. 1, 2 and 3, wherein the triacetin reference measurement is made for instance by measuring the weight loss of the triacetin container 12 using a scale 13. Additionally, an infrared laser measurement device 10*a* is installed at the filter rod 7 in series with the microwave resonator 10 for the purpose of correcting the microwave triacetin signal in the case of a titer change, so that an improved independence of the calibration from the titer is given.

Figure 5:
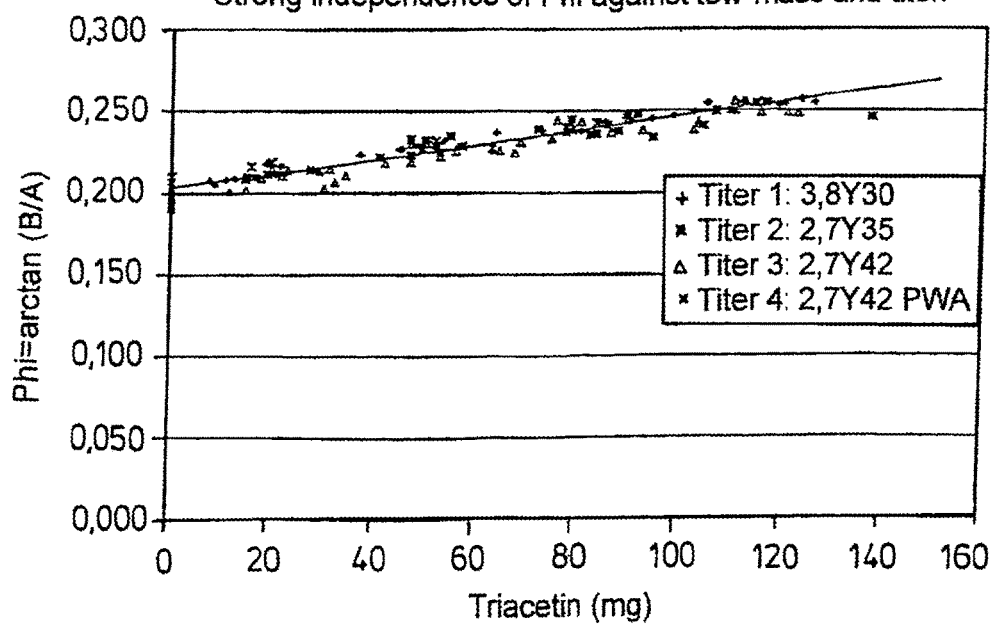
FIG. 5 shows the dependency of the quotient $\Phi=B/A$ of the measurement values A and B for different tow masses and tow titers of triacetin content per filter rod length.

FIG. 5 shows the dependency of the arctan quotient of B and A of triacetin content for four different titer values: there is a clear dependency on the triacetin content with a small increase. The diagram also shows that the quotient of B and A is independent of the filter tow mass and the filter tow titer. At the same time, however, there is a clear dependency on the moisture which is responsible for scattering the measured values about the plotted best fit line. This low dependency on the moisture, which is inherent in the measured values in FIG. 5, can be compensated using the method according to the invention by the periodic comparison to a long-term reference value for the triacetin content, so that through the measurement using a single microwave resonator, the mass of triacetin per length for an endless filter rod can reliably be determined online.

Figure 6:
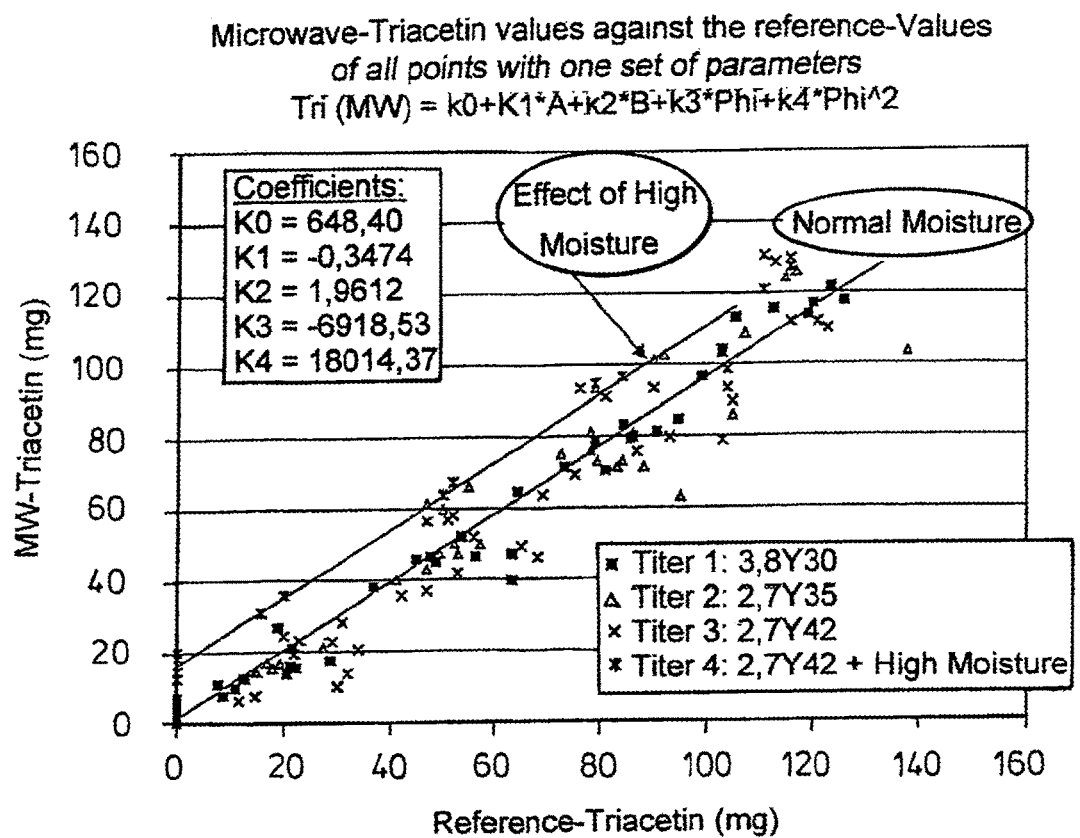
FIG. 6 shows the dependency of the microwave triacetin value per length for different tow masses and tow titers depending on reference triacetin content per length, and the disruptive influence of moisture fluctuations in the filter tow.

FIG. 6 shows the relationship of the triacetin value per length, which results solely from the data A, B and B/A of a microwave resonator at the filter rod, in comparison to the reference triacetin values. The graph shows that different tow masses and different tow titers barely have any influence on the microwave triacetin value. However, the determined triacetin value per length clearly depends on moisture fluctuations in the filter tow. The plotted best fit lines clearly show that by using the reference measurement of the triacetin mass, the influence due to the moisture fluctuations in the filter tow can be reliably eliminated from the measured values.

The method according to the invention makes use of the fact that the variables A and B are linearly dependent on all individual parameters in the endless filter rod. Although the quotient of A and B is independent of the tow mass and the titer, it is however dependent on the triacetin content and the moisture. Thus, the triacetin content can be given as mass per length through a linear combination of the A, B and B/A if the coefficients of these linear combinations are known. These coefficients are determined by a one-time calibration procedure. In this manner, the mass per length of the applied triacetin results from the following expression:

$$m_W = k0 + k1*A + k1*B + k3*(\Phi).$$

Occasionally, the arctan of B/A is referred to also instead of the coefficient $\Phi = B/A$.

Tests have shown that the accuracy the determination of the triacetin content can be increased particularly well by additional higher powers of the quotient $\Phi = B/A$. Thus, for instance, the expression $m_W = k0 + k1*A + k2*B + k3*\Phi + k4*(\Phi)^2$ is already more accurate, however, it requires determining a further coefficient k4 in the calibration process.

The quotient $\Phi = B/A$, or respectively the arctan $\Phi$, or another function of the value $\Phi$ depends only on the content of triacetin and the moisture of the filter rod, so that the moisture value $\Psi$ with a known triacetin value $m_W$ can be expressed as:

$$\Psi = f0 + f1*\Phi + f2*m_W.$$

With a known triacetin mass $m_W$ per filter length and moisture value $\Psi$, the amount of the surface density of the tow content can be determined either from the measured value of A and/or the measured value of B. The variable for the tow content is expressed as mass per length according to the expression:

$$m_T = t0 + t1*A + t2*B + t3*m_W + t4*\Psi,$$

wherein t1 to t4 are constants that are determined by calibration.

The values for triacetin mass, moisture and tow surface mass, determined in the equations above, are instantaneous values of the part of the endless filter rod that is located immediately in the measurement range of the microwave resonator. This measurement range can have a length of 1 mm or more. Consequently, in this manner, a profile of the measurement variables can be measured in the endless filter rod, and a local distribution, of the triacetin for example, can be determined.

A triacetin concentration due to dripping triacetin in the application unit for example, can be detected depending on the sensor based high spatial resolution of the measurement. Such filter rods can, after the cutting procedure, be removed from further processing. Chemical burning of holes in the filter rod ("hot melt" phenomenon) during the production process due to a high triacetin concentration, can be detected in a timely manner, and can be diverted.

Also, an insufficiently adjusted triacetin application due, for example, to incorrect rotational speed of the brushes, can be detected in a timely manner, displayed and corrected.

In addition, moisture fluctuations between different bales can be utilized by a regulation of the tow content so that the finished filter rod, in moisture equilibrium with the environment, has its target weight and its target pressure drop values.

Quality fluctuations in the filter tow, due to filament breakage for example, can be compensated by detecting the filter tow mass per rod so the finished filter rod has its target weight and its target pressure drop value.

The particularly high accuracy also in the values for the profile is attained according to the invention in that there is a long term reference measurement of the triacetin content, in that the triacetin dosing from the triacetin tank is detected by measuring the weight reduction or the reduction of the fill level of the triacetin container over a longer time period. Likewise, the triacetin flow between the storage container and the triacetin application chamber can be determined over a longer time period, wherein this time period must be sufficiently long to average fluctuations in the triacetin flow. At the same time, including the speed of the endless filter rod or the measurement of the rotations of the blade results in that the number of filter rods produced in the same time period is determined, thus, the triacetin content per filter rod can be determined by counting the shaft encoder impulses. On the other hand, the averaged reference triacetin value determined from the supply can be linearly compared with the microwave triacetin value determined during the same time period, and by changing the absolute term k0 with the determination of the triacetin mass, a compensation can be performed so that the triacetin signal acquired from the measurement variables of the microwave resonator concurs with the averaged reference triacetin value from the measurement of the triacetin supply.

Along with the measurement of the long term reference mass per time, which is supplied to the filter tow band, a further signal from an infrared laser measurement device can be referenced that is barely influenced by the triacetin content and the moisture, but in contrast, is significantly influenced by the tow mass. The signal of an infrared laser is formed by deflecting its beam through the scattering on the surface of the individual fiber, and the signal strength after passing through the filter rod is more strongly attenuated when there are more fibers in the beam path. This is a scattering of the beam at the surface of fibers; the moisture or triacetin content of the fiber material have little influence on this scattering. This signal reacts only to variations in the content of the fibers, such as occurs with a change in the type of tow for example. The titer "F-Y-G" of a filter tow bale is defined by the specification of the mass of a fiber F, and the total mass of the band G in grams at a defined length. If the measured intensity S of the scattered laser light is multiplied by the number of fibers, which is expressed by the coefficient G/F, a filter tow signal results that is independent of the titer. Since on the other hand, the laser signal decreases exponentially with increasing tow mass, a linear relationship exists between $\log(S^*G/F)$ and the tow mass, which is independent of triacetin and moisture. Therefore, a further improved mass value $m_W$ per length of the plasticizer can be expressed as:

$$m_W = k0 + k1^*A + k2^*B + k3^*B/A + k4^*\log(S^*G/F).$$

With these variables also, the absolute term k0 is corrected using the averaged reference mass per length determined from the triacetin supply.

The invention claimed is:

1. A method for online measurement of a plasticizer in a filter rod at a filter rod maker, the method comprising:
   measuring a resonance shift (A) and a line broadening (B) of a resonance curve with a microwave resonator at a passing filter rod,
   determining a mass per length of plasticizer from the measurement variables (A, B) of the microwave resonator,
   measuring a reference mass of plasticizer applied per time with the application of the plasticizer onto the filter tow band,
   determining an averaged reference mass per length of plasticizer from the measured mass applied over a time period,
   averaging the values for mass per length of plasticizer, determined using the measurement variables of the microwave resonator, over the same time period in which the reference mass of plasticizer is determined,
   determining a deviation between the averaged reference value for the mass per length and the averaged mass per length, and
   correcting the mass per length of plasticizer determined from the measurement variables of the microwave resonator according to the determined deviation.

2. The method according to claim 1, wherein the time period for determining the reference mass extends at least over the duration of a back and forth run of a lift-off point of the filter tow from a filter tow bale.

3. The method according to claim 2, wherein the averaging of the values determined from the microwave resonator is realized over the time period in which the reference mass is determined.

4. The method according to claim 2, further comprising the following method steps:
   measuring the intensity S of radiation scattered at the filter tow band in the visible or infrared range, and
   determining an additive corrective term, depending on the intensity S, for the mass per length of plasticizer determined from the microwave variables.

5. The method according to claim 4, wherein the mass per length $m_W$ of plasticizer is determined from the following expression:

$$m_W = k0 + k1^*A + k2^*B + P(\Phi) + k3^*\log(S^*G/F)$$

wherein k0, k1, k2 and k3 are coefficients, A is the resonance shift, B is the line broadening, $\Phi$ is the quotient of A and B, P is a polynomial of $\Phi$ or a function of $\Phi$, G is the mass of the filter tow band, and F is the mass of an individual fiber of the filter tow band of a defined length.

6. The method according to claim 1, further comprising the mass per length $m_W$ of plasticizer is determined according to:

$$m_W = k0 + k1^*A + k2^*B + P(\Phi),$$

wherein A is the resonance shift, B is the line broadening, k0, k1, k2 are coefficients, $\Phi$ is the quotient of A and B, and P is a polynomial depending on $\Phi$ or a function of $\Phi$.

7. The method according to claim 6, wherein the value of the constant k0 is corrected by the value of the determined deviation between the averaged triacetin content from the microwave measurements and the reference triacetin content of the reference measurement.

8. The method according to claim 1, further comprising the plasticizer is applied from a storage container onto the filter tow band, and the weight reduction of the storage container is measured for determining the reference mass per length of plasticizer.

9. The method according to claim 1, further comprising the plasticizer is applied from a storage container onto the filter tow band and the change of the fill level of the storage container is measured for determining the reference mass per length of plasticizer.

10. The method according to claim 1, further comprising the plasticizer is applied from a storage container onto the filter tow band and the volume fed into the feed line is measured for determining the reference mass per length of plasticizer.

11. The method according to claim 1, further comprising the average mass per length of plasticizer is determined continuously.

12. The method according to claim 1, further comprising the deviation is determined continuously.

13. The method according to claim 1, further comprising one of claims 1 to 12, characterized in that the mass determined from the measurement variables of the microwave resonator is corrected continuously.

14. The method according to claim 1, further comprising a moisture value for the filter rod is determined depending on the measurement variables of the microwave resonator and the corrected value for the mass per length of plasticizer.

15. The method according to claim 14, wherein a moisture value $\Psi$ is determined according to:

$$\Psi = f0 + f1^*\Phi + f2^*m_W$$

wherein f0, f1, f2 are coefficients, $\Phi$ is the quotient from the resonance shift A and the line broadening B, or a function of the quotient, and $m_W$ is the corrected value for the mass per length of plasticizer.

16. A device for an online measurement of the content of plasticizer in a filter rod of the tobacco processing industry, comprising:
   a microwave resonator that measures a resonance shift (A) and a line broadening (B) of a resonance curve of the passing filter rod,
   a reference measurement device that measures a reference mass per time of a plasticizer applied onto the filter tow band, and
   an evaluation unit supplied with the measured values (A) and (B) of the microwave resonator and the reference measurement device, and which
      determines a mass per length of plasticizer from the measured values of the microwave resonator,
      determines an averaged reference mass per length from the measured values (A) and (B) of the reference measurement device, and
      corrects the mass per length of plasticizer based on a deviation from the averaged reference mass per length of plasticizer.

17. The device according to claim 16, wherein a scale is provided as a reference measurement device that detects a reference mass change per time in a storage container for the plasticizer.

18. The device according to claim 16, wherein the reference measurement device detects the change of the fill level of the storage container.

19. The device according to claim 16, further comprising the reference measurement device has a volume flow meter that detects the volume per time during application of the plasticizer.

20. The device according to claim 16, wherein a laser and an intensity sensor are provided for laser light scattered at the filter tow band, wherein the evaluation unit corrects the mass per length of plasticizer depending on the intensity of the scattered laser light.

\* \* \* \* \*